United States Patent
Barnett et al.

[11] Patent Number: 5,884,624
[45] Date of Patent: *Mar. 23, 1999

[54] RESPIRATORY MASK FACIAL SEAL

[75] Inventors: Shari S. Barnett, Pittsburgh; Patrick M. Handke, Monroeville; Kristine K. Sabo, New Kensington; Eugene N. Scarberry, Trafford, all of Pa.

[73] Assignee: Respironics, Inc., Pittsburgh, Pa.

[*] Notice: The term of this patent shall not extend beyond the expiration date of Pat. No. 5,647,357.

[21] Appl. No.: 832,267

[22] Filed: Apr. 3, 1997

Related U.S. Application Data

[63] Continuation of Ser. No. 525,404, Sep. 8, 1995, Pat. No. 5,647,357.

[51] Int. Cl.$^6$ .................................................. A62B 18/08
[52] U.S. Cl. ............................. 128/206.24; 128/206.23; 128/206.25; 128/206.14
[58] Field of Search .................. 128/206.24, 206.23, 128/206.21, 206.25, 206.14, 201.18, 858

[56] References Cited

U.S. PATENT DOCUMENTS

| | | | |
|---|---|---|---|
| 2,254,854 | 9/1941 | O'Connell | 128/206.26 |
| 2,625,155 | 12/1953 | Engelder | 128/206.24 |
| 2,837,090 | 6/1958 | Bloom et al. | 128/206.24 |
| 2,917,045 | 12/1959 | Schildknecht et al. | 128/206.24 |
| 2,931,356 | 4/1960 | Schwarz | 128/206.24 |
| 4,369,284 | 1/1983 | Chen | 524/476 |
| 4,665,570 | 5/1987 | Davis | 2/428 |
| 5,181,506 | 1/1993 | Tardiff, Jr. et al. | 128/201.22 |
| 5,334,646 | 8/1994 | Chen | 524/474 |
| 5,343,878 | 9/1994 | Scarberry et al. | |
| 5,647,357 | 7/1997 | Barnett et al. | 128/206.24 |
| 5,662,101 | 9/1997 | Ogden et al. | 128/206.24 |

FOREIGN PATENT DOCUMENTS 0618807  4/1961  Canada ............................. 128/206.24

OTHER PUBLICATIONS

S.F.C. Stewart, V. Palmieri and G.V.B. Cochran, "Wheelchair Cushion Effect on Skin Temperature, Heat Flux, and Relative Humidity", Arch. Phys. Med. Rehabil., vol. 61, pp. 229–233 (May 1980).

*Primary Examiner*—John G. Weiss
*Assistant Examiner*—V. Srivastava
*Attorney, Agent, or Firm*—Reed Smith Shaw & McClay

[57] ABSTRACT

An improved flexible respiratory mask facial seal, as well a respiratory mask incorporating such seal. The facial seal comprises an annular member including a peripheral sidewall bounded by an inner end and an outer end generally opposite the inner end. The inner end is adapted for attachment to the shell or body portion of a respiratory mask and the outer end defines a contoured sealing surface adapted for confronting sealing engagement with a user's face. The annular member is formed of a gel substance possessing resilience characteristics corresponding to those of human fat tissue. Preferably, the annular member is encapsulated in a thin, pliable, membranous covering to enhance the durability and washability of the facial seal. Because the facial seal simulates the resiliency of human fat tissue, the user experiences the sensation of a natural substance against his skin when the mask is donned.

20 Claims, 5 Drawing Sheets

Fig. 5

RESPIRATORY MASK FACIAL SEAL

This application is a continuation of application Ser. No. 08/525,404, filed on Sep. 8, 1995, now U.S. Pat. No. 5,647,357 the contents of which are hereby incorporated by reference.

FIELD OF THE INVENTION

The present invention relates in general to respiratory masks and, more particularly, to respiratory masks having flexible seals adapted to receive portions of a user's face for preventing leakage of gas being supplied to the user.

BACKGROUND OF THE INVENTION

A variety of respiratory masks are known which have flexible seals that cover the nose and/or mouth of a human user and are designed to create a continuous seal against the user's face. Because of the sealing effect that is created, gases may be provided at positive pressure within the mask for consumption by the user. The uses for such masks range from high altitude breathing (i.e., aviation applications) to mining and fire fighting applications, to various medical diagnostic and therapeutic applications.

One requisite of such respiratory masks has been that they provide an effective seal against the user's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

The prior art includes several types of respiratory face masks for the types of applications mentioned above. Perhaps the most common type of mask incorporates a smooth sealing surface extending around the periphery of the mask and exhibiting a generally uniform (i.e., predetermined or fixed) seal surface contour which is intended to be effective to seal against the user's face when force is applied to the mask with the smooth sealing surface in confronting engagement with the user's face. The sealing surface typically consists of an air or fluid filled cushion, or it may simply be a molded or formed surface of a resilient seal element made of an elastomer such as plastic, rubber, silicone, vinyl or foam. Such masks have performed well when the fit is good between the contours of the seal surface and the corresponding contours of the user's face. However, if the seal fit is not good, there will be gaps in the seal-to-face interface and excessive force will be required to compress the seal member and thereby attain a satisfactory seal in those areas where the gaps occur. Such excessive force is unacceptable as it produces high pressure points elsewhere on the face of the user where the mask seal contour is forcibly deformed against the face to conform to the user's facial contours. This will produce considerable user discomfort and possible skin irritation and breakdown anywhere the applied force exceeds the local perfusion pressure, which is the pressure that is sufficient to cut off surface blood flow. Ideally, contact forces should be limited between the mask and the user's face to avoid exceeding the local perfusion pressure even at points where the mask seal must deform considerably.

The problem of seal contact force exceeding desirable limits is even more pronounced when the positive pressure of the gas being supplied is relatively high or is cyclical to high levels. Since the mask seals by virtue of confronting contact between the mask seal and the user's face, the mask must be held against the face with a force sufficient to seal against leakage of the peak pressure of the supplied gas. Thus, for conventional masks, when the supply pressure is high, headstraps or other mask restraints must be tightly fastened. This produces high localized pressure on the face, not only in the zone of the mask seal but at various locations along the extent of the retention straps as well. This too will result in severe discomfort for the user after only a brief time. Even in the absence of excessive localized pressure points, the tight mask and headstraps often may become extremely uncomfortable and user discomfort may well cause discontinued cooperation with the regimen.

Examples of respiratory masks possessing continuous cushion sealing characteristics of the type just described are provided in U.S. Pat. Nos. 2,254,854 and 2,931,356.

U.S. Pat. No. 5,181,506 describes a protective gas mask for military applications. The mask includes a three-layer face piece, the central layer of which is a thick layer of relatively stiff material having preformed V-shaped channels. The channels are "overfilled" with a gel or both gel and compressed air so as to create bulges in an inner face-contacting layer which are adapted to seal against the contours of a user's face. The inherent stiffness of the central layer in combination with the structural rigidity provided by the V-shaped channels, especially when overfilled with gel/air, results in a comparatively unyielding facial seal. Indeed, the mask is deployed in combination with a tightly fitting hood in order to draw the face piece firmly against the user's head to thereby generate the desired facial seal. As will be appreciated, the comfort afforded such a construction is quite limited and certainly not appropriate for those applications, such as respiratory therapy situations, where a user must occasionally wear a mask for prolonged periods of time.

Several classes of cushion materials, including gels and foams, were analyzed in a study by S. F. C. Stewart, V. Palmieri and G. V. B. Cochran, Arch. *Phys. Med. Rehabil.*, Vol. 61, (May 1980). That study compared the relative advantages and disadvantages of such cushion materials when used as wheelchair cushions, specifically the effects of such materials on skin temperature, heat flux and relative humidity at the skin-cushion interface. Each of these factors, along with applied pressure in excess of local perfusion pressure, has been identified as a contributor to breakdown of skin tissue at the skin-cushion interface.

In that study, foam cushions were reported to increase skin temperatures by several degrees after a few hours of use. This was suggested to be a result of the comparatively low heat flux characteristics of foam materials. That is, the foam materials and the air entrapped within them tend to be poor absorbers and conductors of heat. Conversely, gel pads, as a group, showed a considerably higher heat flux than foam, sufficient in fact to maintain skin temperatures relatively constant after several hours of use. The sole benefit of foam versus gel reported in the study was that foams produced lesser relative humidity than gels at the skin-cushion interface. This was attributed to the open cell structure of the foams which provide a pathway through which moisture can diffuse. This seeming advantage is somewhat problematic, however, in that open cell foam tends to promote bacteria growth when exposed to perspiration. Bacteria, in turn, contaminates the foam thereby considerably hindering its useful service life.

These and other detrimental characteristics have been observed as well in the foam-type respiratory mask seals discussed above. Hence, apart from generally failing to provide optimum sealing with respect to a user's face, the inherent qualities of foam mask seals have been linked to skin irritation and breakdown, particularly at some of the more prominent facial contours such as the cheek bones and bridge of the nose.

Moreover, whether air, fluid or, in the case of U.S. Pat. No. 5,181,506, gel filled, or whether formed as an elastomer such as foam, plastic, rubber, silicone and the like, the resiliency or recoil characteristics of presently available cushion type respiratory mask seals have not been well suited to form an effective seal with the topography of the user's face in the absence of considerable headstrap tensile forces. The present inventors have discovered that headstrap tensile forces and, therefore, the compressive forces exerted by the mask against a user's face, can be reduced substantially with respect to existing cushion-type respiratory masks when the mask cushion is fabricated from materials having recoil characteristics analogous to that of human fat. Such a cushion has been found to behave much like natural biological tissue and tends to conform naturally to a user's face under the influence of very low headstrap forces. The present inventors have also discovered that, in addition to their other aforementioned advantages, gel materials can be produced that simulate the recoil properties of human fat tissue.

An advantage exists, therefore, for a respiratory mask facial seal comprising a seal cushion formed of a gel that affords an effective yet comfortable and non-damaging seal with a user's facial contours.

SUMMARY OF THE INVENTION

The present invention provides an improved flexible respiratory mask facial seal, as well a respiratory mask incorporating such seal, which reliably and comfortably seals the facial contours of a user.

The facial seal comprises an annular member including a peripheral sidewall bounded by an inner end and an outer end generally opposite the inner end. The inner end is adapted for attachment to the shell or body portion of a respiratory mask and the outer end defines a contoured sealing surface adapted for confronting sealing engagement with a user's face.

The annular member is formed of a gel substance such as a viscoelastic polyurethane polymer possessing resilience or recoil characteristics corresponding to those of human fat tissue. The annular member may be deployed with or without a protective covering. In the absence of such a covering, the inherent tacky quality of the gel substance serves to enhance adhesion of the facial seal to the user's face. Alternatively, if tackiness is not desired, the surface of the annular member may be covered with a coating of powdered talc, silicone or similar biocompatible material. Most preferably, however, the annular member is encapsulated in a thin, pliable, membranous covering to enhance the durability and washability of the facial seal.

Because the facial seal simulates the recoil characteristics of human fat tissue, the user experiences the sensation of a natural substance against his skin when the mask is donned. Consequently, a mask provided with such a cushion can be comfortably urged into continuous sealing engagement with a user's face with less headstrap tension than other masks heretofore known in the art. Furthermore, the fat-like qualities of the gel cause the gel to effectively fill gaps and mold to other facial contours thereby minimizing leakage of pressurized gas supplied to the mask. The gel material also serves to efficiently dissipate heat while resisting the bacteria growth associated with foam type mask seals.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings, wherein.

DETAILED DESCRIPTION OF THE INVENTION

Figure 1:
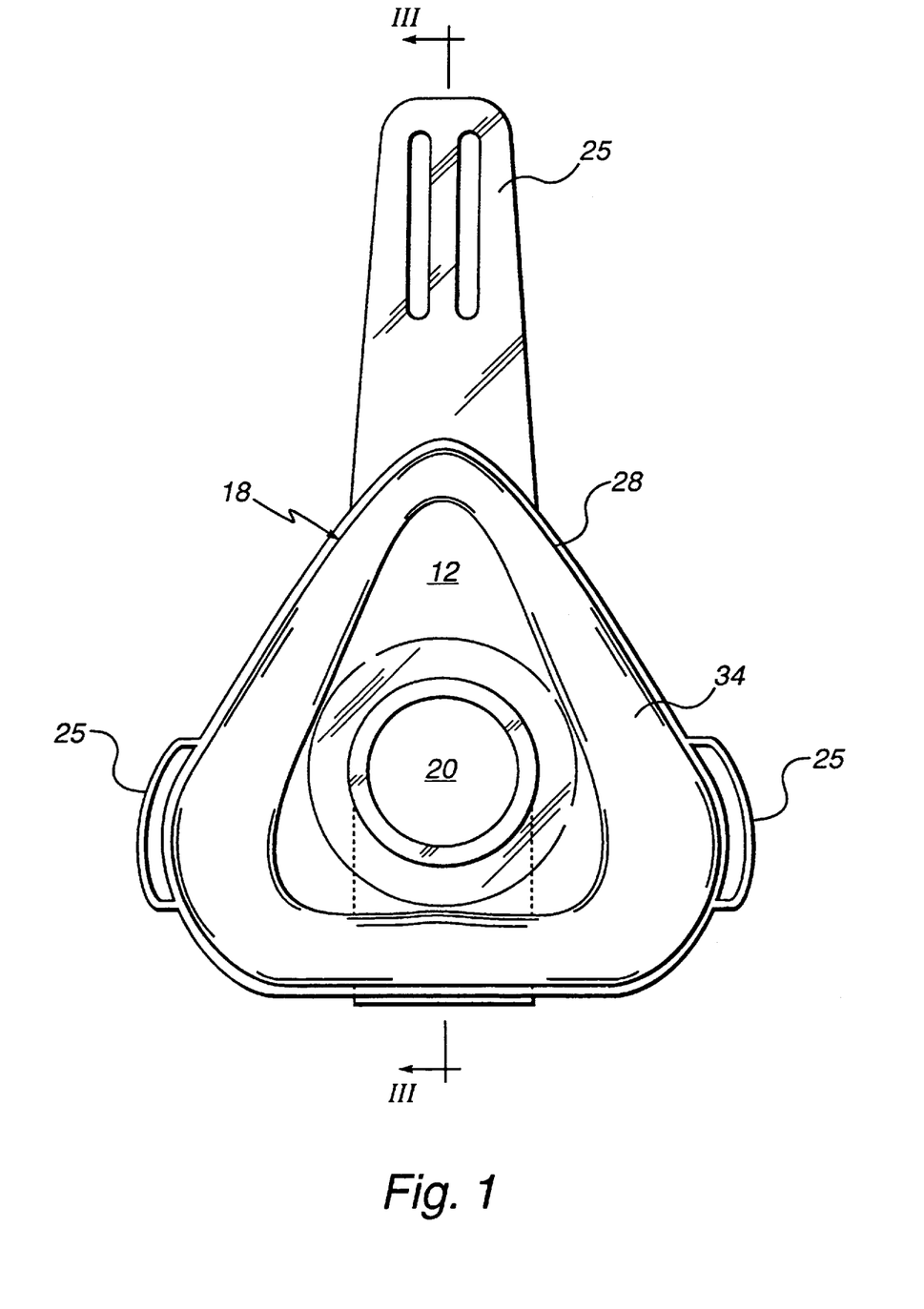
FIG. 1 is a front elevation view of a respiratory mask including a first preferred embodiment of a facial seal constructed according to the present invention.
Figure 2:
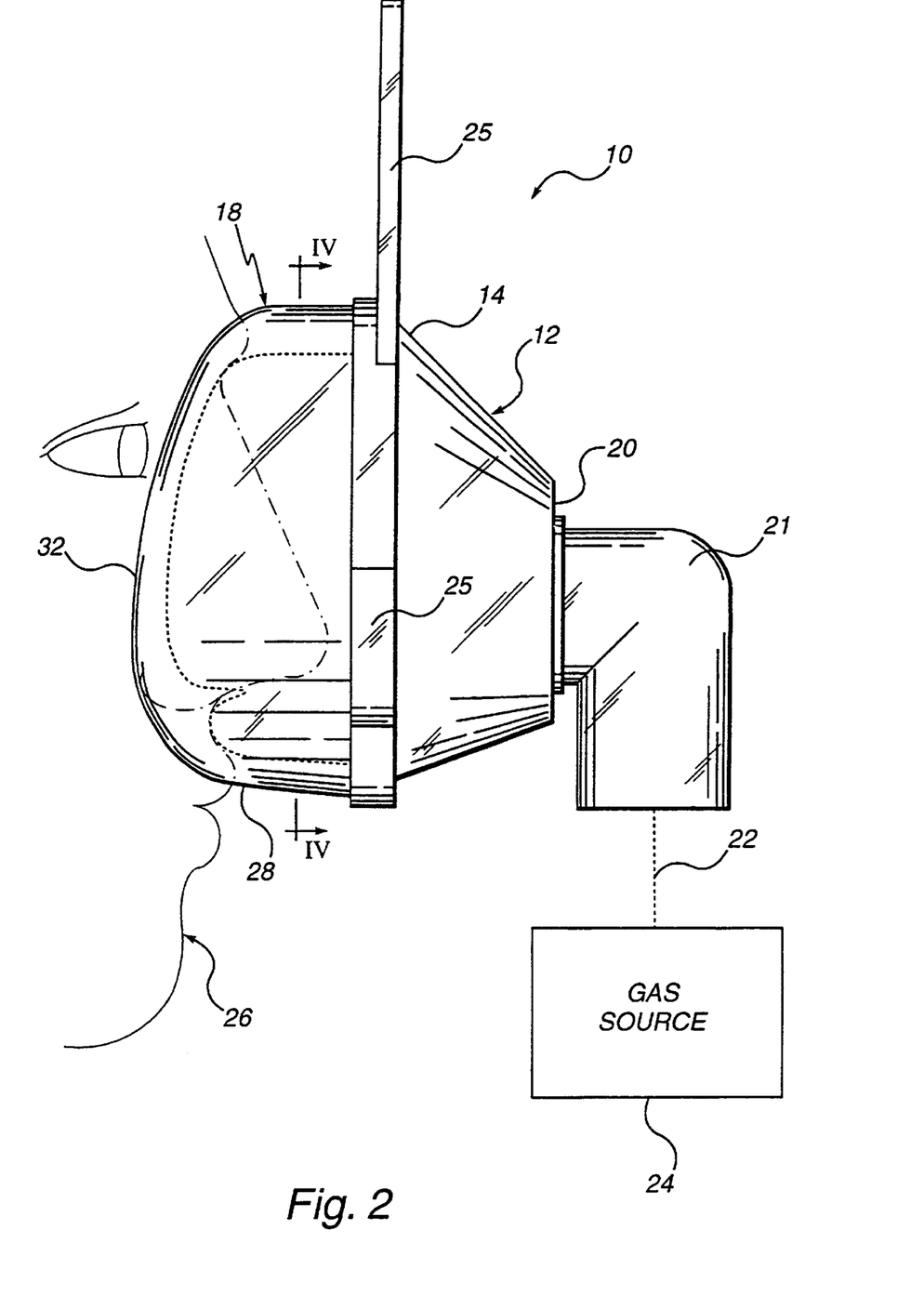
FIG. 2 is a side elevation view of the respiratory mask of FIG. 1 when in confronting, sealing engagement with a user's face, the respiratory mask being schematically depicted in communication with a source of respiratory gas.

Referring initially to FIGS. 1 and 2, there is generally indicated at 10 a respiratory mask including a shell or body portion 12 having an open side 14 that defines an annular surface 16 (perhaps most clearly illustrated in FIG. 3) to which is sealingly affixed a facial seal 18 constructed according to a first presently preferred embodiment of the instant invention. The mask body portion 12 is preferably, although not necessarily, a generally rigid formed structural shell, whereas facial seal 18 is a flexible, resilient unitary member which will be described in greater detail hereinafter.

Body portion 12 also defines an opening 20 to which there may be attached a fluid coupling means such as a swivel coupling 21 or other suitable means. The opening 20 and any intervening coupling means 21 connect mask 10 via conduit means (represented by dashed line 22) to a source of gas 24, e.g., a blower of other suitable means for providing a flow of pressurized breathing gas, for administration of the gas to a user 26. The mask shown is a nasal mask which accommodates the nasal regions of the user's face. It is to be understood, however, that the invention also contemplates a full face or oral/nasal mask that accommodates both the mouth and nose of a user. As is conventional, mask shell 12 also preferably includes fastening means such as tabs 25 or the like to which may be connected suitable adjustable retention straps (not illustrated) for retaining the mask with respect to the user's face.

Seal 18 includes a solid yet highly resilient and self-sustaining compressible annular member 27 comprising a peripheral wall portion 28 having an annular base or inner end 30 (FIG. 3) configured substantially similar to the annular surface 16 of shell 12 to which it may be fixedly attached. Peripheral wall portion 28 further establishes an outer end 32 generally opposite inner end 30. The outer end 32 defines a generally annular contoured sealing surface 34 adapted for confronting, sealing engagement with a user's face. As will be more fully developed later herein, the contour of sealing surface 34 closely approximates the surface contour of a user's facial structure in the areas of the bridge of the nose, the cheeks adjacent the nose, the space intermediate the nose and upper lip, and the intervening areas contiguous to these. For a full face mask (not illustrated) the sealing surface 34 would be contoured to accommodate the user's chin in lieu of the area intermediate the nose and upper lip. In either case, variation in user facial structure, especially in the area of the bridge of the nose, for example, makes considerable seal flexibility necessary to accommodate the many different facial contours likely to be encountered.

Figure 3:
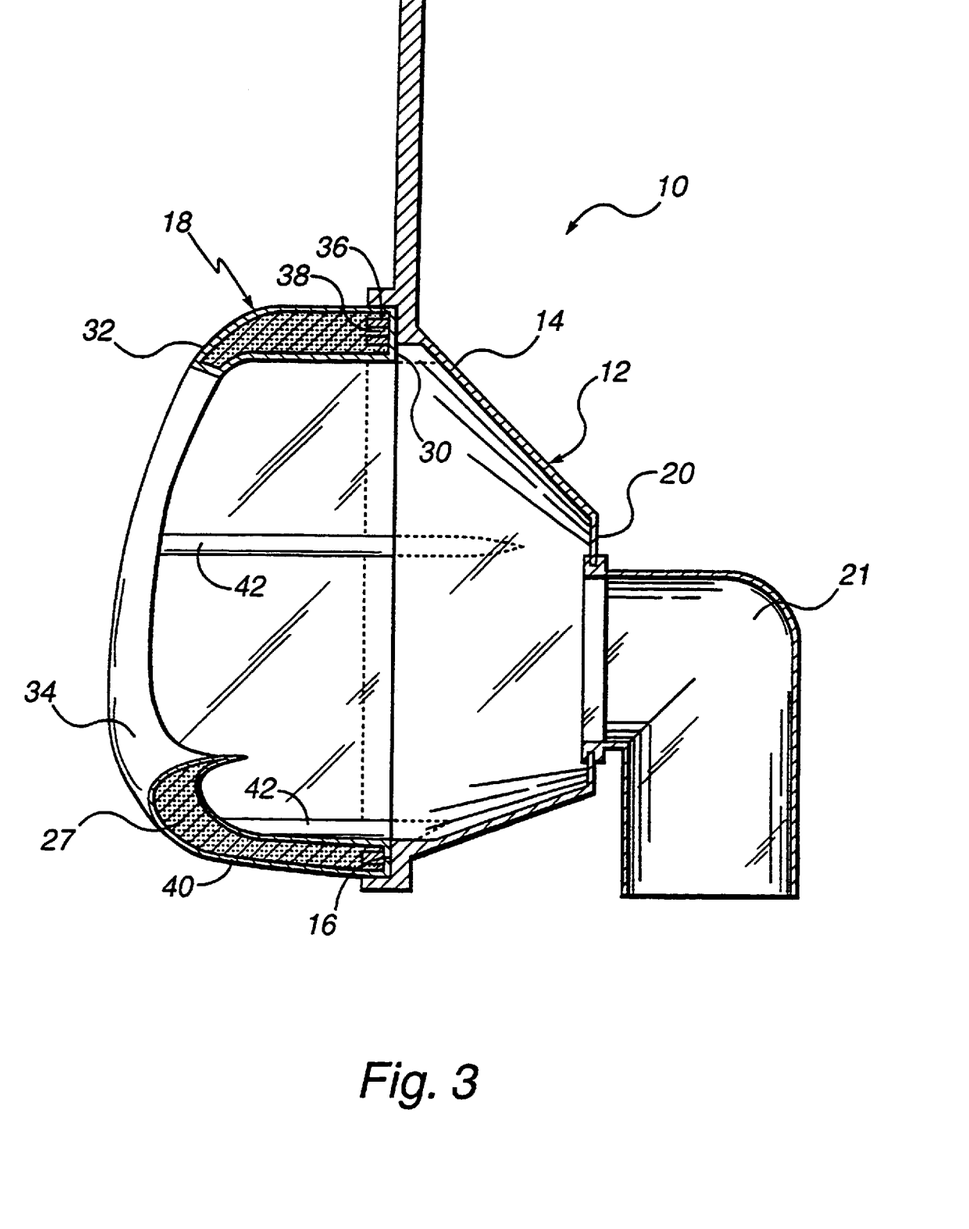
FIG. 3 is a cross-section taken along line III—III of FIG. 1.
Figure 4:
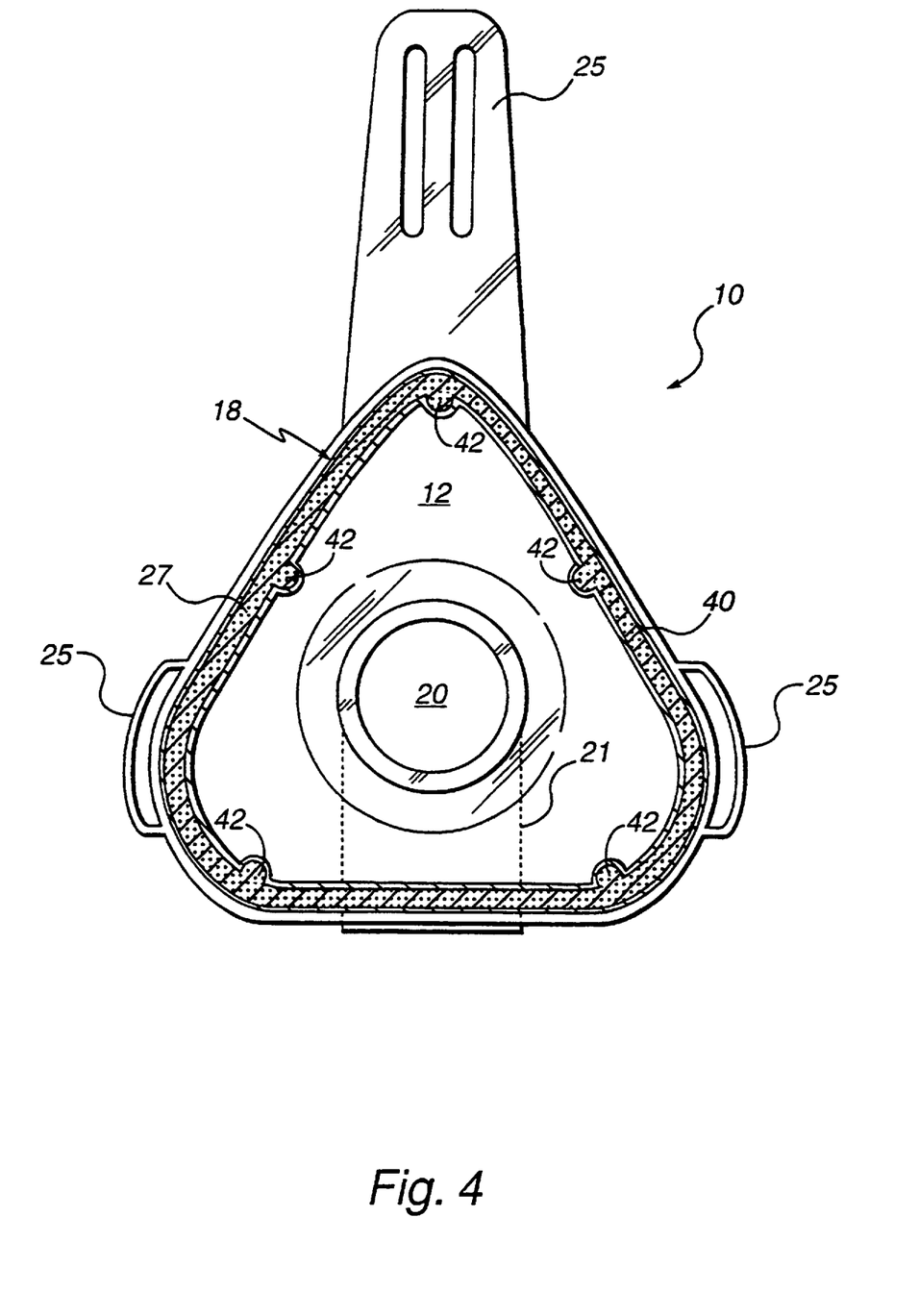
FIG. 4 is a cross-section taken along line IV—IV of FIG. 2.

FIGS. 3 and 4 reveal in more detail the respiratory mask seal 18. In accordance with the present invention, at least the seal or face-contacting portion or, more preferably (as illustrated), substantially the entirety of the annular member 27 is formed from a gel substance such as a viscoelastic polyurethane polymer possessing resilience or recoil characteristics corresponding substantially to those of human fat tissue. More specifically, the facial seal 18 including the annular member 27 preferably has a resiliency, as defined by durometer measured on the Shore 00 scale which is used to gauge the resiliency of very soft resilient materials, of about 10 or softer and, most preferably, about 0. Such resiliency, corresponds substantially to that of human fat tissue which also exhibits a durometer reading of 0 on a Shore 00 scale. In respect to the facial seal embodiment shown in FIGS. 1 through 4, the durometer of facial seal 18. corresponds to the resultant durometers of the annular member 27 and its later described protective covering (whose durometer is essentially negligible because of the thinness and pliability of the covering). As for the facial seal illustrated in FIG. 5 wherein the annular member 27 has no protective covering, the durometer of the facial seal is that of the annular member.

Although inherently capable of filling spatial voids, human fat tissue has negligible structural integrity and may not be self-sustaining. Consequently, any respiratory mask facial seal possessing structural characteristics essentially identical to fat would be impractical from a usage standpoint. That is, if a facial seal were fabricated from a material structurally indistinguishable from human fat tissue in terms of resiliency, it may tend to sag into an amorphous shape under the influence of gravity and thus would not effectively conform to the contours of a user's face even if headstrap tension was quite high. It will be appreciated, therefore, that a properly designed facial seal must substantially but not identically mimic human fat tissue from a structural, particularly resiliency, perspective. Stated differently, the facial seal must exhibit some measurable recoil "memory" whereby it is structurally self-sustaining, capable of gently conforming to the topography of a user's face under the influence of low headstrap tensile forces, resistant to distorting gravitational effects and self-restorable to its original configuration when removed from contact with the user's face. It must also be resistant to distortion due to positive gas pressure supplied to the mask. To simultaneously achieve these and other beneficial properties, the annular member 27 according to the present invention is preferably formed from a gel substance that, while virtually indistinguishable from human fat tissue when measured on the Shore 00 scale, exhibits a resilency or durometer on the Shore 000 scale (which scale is used to measure the resiliency of extremely soft resilient materials) of from about 20 to about 45. By comparison, human fat tissue registers a durometer of about 10 on the Shore 000 scale.

The annular member 27 may be fabricated by conventional molding techniques. For example, liquid polyurethane polymer including any plasticizers and other modifiers necessary to achieve desired finished product properties is poured or injected into an appropriately configured mold. The polymer is then permitted to cure, either with or without the application of heat depending upon the specific composition and setting characteristics of the polymer, until the product achieves its desired solid gel form. Because the polymer of the annular member does not have sufficient structural integrity to reliably adhere directly to the body portion 12 of the mask, the facial seal 18 also preferably comprises attachment means 36 which may be integrally molded into the inner end 30 of the annular member during its formation. Attachment means 36 is desirably constructed as a substantially rigid annular ring having shape corresponding to that of the inner end 30 and a wall thickness less than or equal to that of the wall thickness of the peripheral wall portion 28. At minimum, however, attachment means 36 should comprise a member less resilient than the gel substance of the annular member. To enhance bonding of the attachment means 36 to the annular member 27, the attachment means desirably includes anchorage means 38. The anchorage means may comprise spaced apart formations of the attachment means defining openings or similar structures into or around which the fluid polymer may flow and ultimately cure during formation of the annular member.

Annular member 27 also preferably comprises a plurality of integral bosses 42 molded into the peripheral wall portion 28 during formation of the annular member which extend from the inner end 30 toward the outer end 32. Bosses 42 provide gentle structural support to the annular member and promote uniform compression of the annular member when such member is in contact with a user's face. The bosses should be symmetrically disposed about the peripheral wall portion and preferably correspond in number and location to the anchorage means 38. As shown in FIG. 3, a presently preferred construction envisions five such bosses 42 corresponding to five anchorage means 38.

As previously mentioned, the presently preferred embodiment of facial seal 18 contemplates that the annular member 27 be covered by a protective covering. Such covering means is identified by reference numeral 40 in the drawing figures. The covering means functions to increase the durability of the annular member while also permitting easy cleaning of the facial seal. Covering means 40 must satisfy several physical criteria. It must, inter alia: (1) resist tearing and puncturing, (2) tightly conform to the annular member 27 without changing or deforming the contours thereof, (3) be chemically compatible with the annual member, (4) be biocompatible and non-irritating to a user's skin, and (5) be sufficiently thin and supple such that its presence has a negligible impact on the resultant durometer of the facial seal 18. In this regard, covering means 40 preferably comprises a thin (approximately 2 to 10 mils thick) flexible plastic film. Urethane has been found to be preferable for this particular purpose as such material meets not only the objectives of the present invention but is also comparatively inexpensive and easy to apply to the surface of the annular member 27. The covering means 40 may be applied to the annular member by any suitable process. For instance, liquid urethane may be applied by spraying or dipping and then permitted to cure. Preferably, however, the urethane is prefabricated by vacuum forming so as to produce a skin of controllable and uniform thickness which is subsequently vacuum formed to the annular member using contentional techniques.

Once the facial seal 18 is fully assembled, it may be attached to the body portion 12 of a respiratory mask by coating the inner end 30 of the facial seal and/or the annular seating surface 16 of the mask body portion 12 with a suitable adhesive and then pressing the inner end 30 into abutment with the seating surface 16 whereupon the adhesive is allowed to cure.

Figure 5:
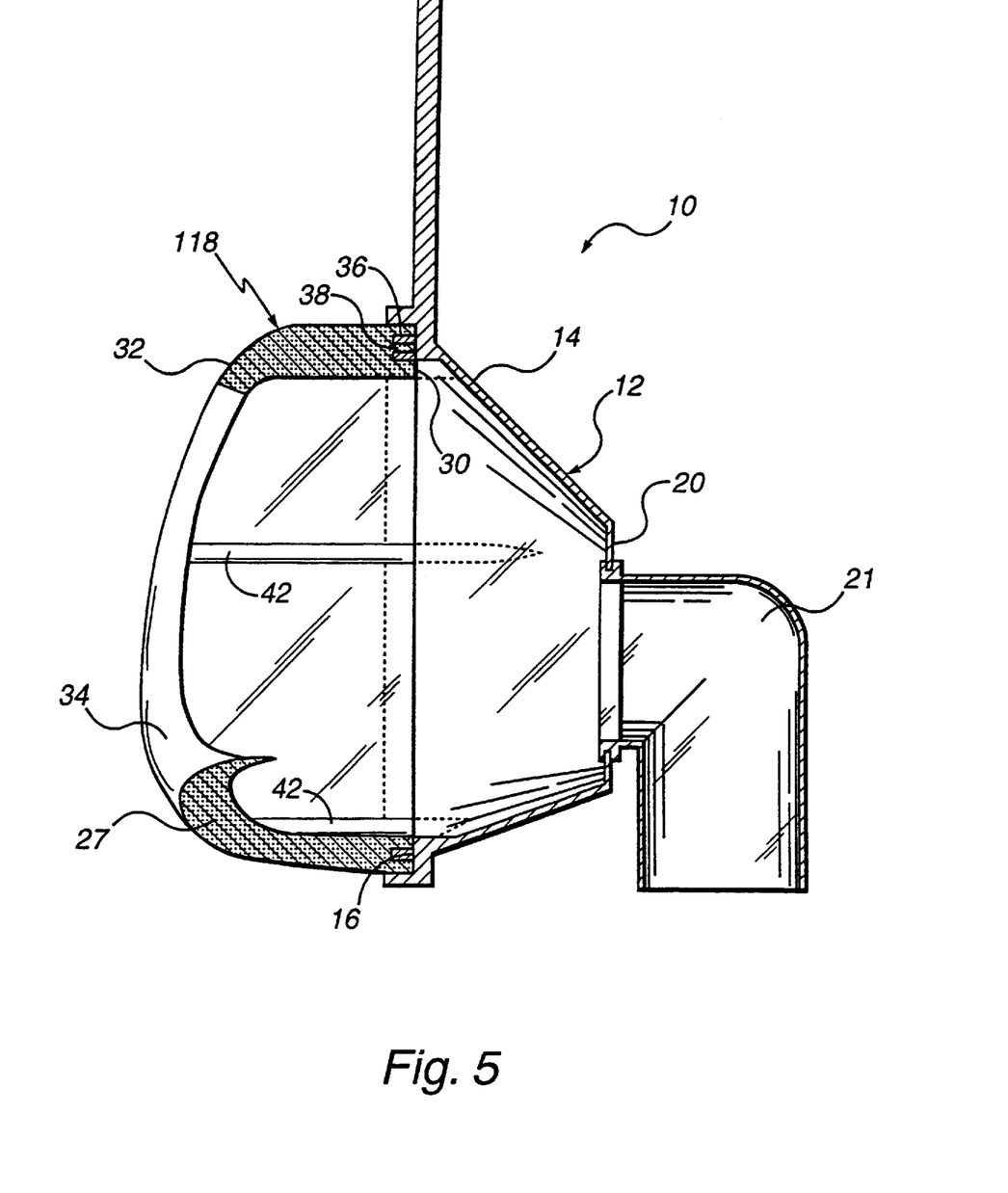
FIG. 5 is an elevational cross-section view similar to FIG. 3 of a respiratory mask including a further preferred embodiment of a facial seal constructed according to the present invention.

In FIG. 5, wherein like references designate like or corresponding parts to those previously discussed, there is illustrated a further preferred embodiment of the facial seal of the present invention which is identified herein by reference numeral 118. Facial seal 118 differs from facial seal 18 essentially in that the annular member 27 thereof has no protective covering means on its outer surface. In all other material respects, facial seal 118 is constructed and functions substantially identically to facial seal 18.

The exposed surface of the annular member 27 of is tacky. As such, the inherent tackiness of the contoured sealing surface 34 of the annular member may thus be used to the user's advantage by enhancing adhesion of the facial seal to the user's face. In the alternative, if tackiness is not desired, the surface of the annular member 27 of facial seal 118 may be covered with a coating of powdered talc, silicone or similar biocompatible material.

As presently contemplated, the wall thickness of the peripheral wall portion 28 of the annular seal member 27 of the facial seals 18 and 118, excluding bosses 42, preferably ranges from about 0.2 to 0.3 inches. The weight of the facial seals 18, 118 depending on the size of mask bodies 12 with which they are used, ranges from about 1 to 2 ounces, a weight which has been discovered to be virtually unnoticeable to patients who have worn masks constructed according to the present invention in clinical tests. Furthermore, the fat-like resiliency qualities of the gel material which forms the annular member 27 creates in the wearer a comparatively cool and natural tactile sensation when the facial seal is in contact with the user's face. And, much like human fat tissue would perform, the facial seals 18, 118 effectively fill gaps and mold to the user's facial topography thereby minimizing leakage of gas supplied to the mask. Indeed, experimental testing has shown that respiratory masks fitted with facial seals in accordance with the present invention exhibit minimal gas leaks with headstrap tensile forces of 3 pounds or less, a value substantially less than related masks presently known in the art. The facial seals described herein thus enable respiratory masks to be worn by users for prolonged periods with little or no measurable discomfort. This phenomenon is especially important to users who must wear respiratory masks for extended periods such as patients undergoing respiratory therapy. Such individuals find that because of the comfort afforded by the facial seals 18, 118, their compliance with the respiratory treatment increases and the therapeutic benefits of the treatment are more fully realized.

As an alternative to the embodiments discussed above, it is also contemplated that a respiratory mask of the present invention may be constructed as a one-piece member rather than as a separate facial seal joined to a mask body. In such case, the respiratory mask may be fabricated as a unitary member formed from substances of increasingly softer durometers, as considered in a direction from that portion of the mask corresponding to the mask body toward that portion corresponding to the facial seal, such that the softest materials, comprising the previously discussed gel substance and possessing the resiliency characteristics described hereinabove, would constitute the seal or face-contacting portion of the annular member.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A facial seal comprising:
   a seal portion operatively coupled to said mask body for sealing engagement with a face of a human user, said seal portion having a recoil characteristic substantially corresponding to that of human fat tissue, and including a property of recoiling back to substantially its original shape when not stressed.

2. The facial seal of claim 1 wherein said seal portion comprises a peripheral wall portion having an inner end and an outer end opposite said inner end, said inner end being attachable to a body of a respiratory mask and said outer end having a contoured sealing surface for sealing engagement with said face of said human user.

3. The facial seal of claim 2 further comprising an attaching means, having a shape corresponding to that of said inner end of said peripheral wall portion, for attaching said inner end to said body of said respiratory mask.

4. The facial seal of claim 3 wherein said attaching means comprise a member less resilient than said seal portion connected to said seal portion.

5. The facial seal of claim 4 wherein said less resilient member comprises means for anchoring said seal portion to said less resilient member.

6. The facial seal of claim 5 wherein said anchoring means comprise spaced apart openings.

7. The facial seal of claim 6 wherein said peripheral wall portion further comprises means for strengthening said peripheral wall portion.

8. The facial seal of claim 7 wherein said strengthening means comprise a plurality of spaced apart bosses, each of said bosses disposed opposite to each of said spaced apart openings of said anchoring means.

9. A facial seal comprising:
   an annular peripheral wall portion having an inner end and an outer end opposite said inner end, said inner end being attachable to a body of a respiratory mask and said outer end including a seal portion having a contoured sealing surface for sealing engagement with a user's face, at least said seal portion being formed from a gel substance having a resiliency substantially corresponding to that of human fat tissue, said gel substance including a property of recoiling back to substantially its original shape when not stressed; and
   an attaching means, having a shape corresponding to that of said inner end of said peripheral wall portion, for attaching said inner end to said body of said respiratory mask.

10. The facial seal of claim 9 wherein said attaching means comprise a member less resilient than said gel substance connected to said gel substance.

11. The facial seal of claim 10 wherein said less resilient member comprises means for anchoring said gel substance to said less resilient member.

12. The facial seal of claim 11 wherein said anchoring means comprise spaced apart openings.

13. The facial seal of claim 12 wherein said peripheral wall portion further comprises means for strengthening said peripheral wall portion.

14. The facial seal of claim 13 wherein said strengthening means comprise a plurality of spaced apart bosses, each of said bosses disposed opposite to each of said spaced apart openings of said anchoring means.

15. A respiratory mask comprising:

a respiratory mask body;

a flexible, resilient respiratory mask facial seal for engagement with a face of a human user to form a sealed interface encompassing a predetermined portion of such user's face, said facial seal comprising an annular peripheral wall portion having an inner end and an outer end opposite said inner end, said inner end being attachable to said respiratory mask body and said outer end including a seal portion having a contoured sealing surface for sealing engagement with a user's face, at least said seal portion being formed from a gel substance having a resiliency substantially corresponding to that of human fat tissue, said gel substance including a property of recoiling back to substantially its original shape when not stressed; and an attaching means, having a shape corresponding to that of said inner end of said peripheral wall portion, for attaching said inner end to said respiratory mask body.

16. The respiratory mask of claim 15 wherein said attaching means comprise a member less resilient than said gel substance connected to said gel substance.

17. The respiratory mask of claim 16 wherein said less resilient member comprises means for anchoring said gel substance to said less resilient member.

18. The respiratory mask seal of claim 17 wherein said anchoring means comprise spaced apart openings.

19. The respiratory mask of claim 18 wherein said peripheral wall portion further comprises means for strengthening said peripheral wall portion.

20. The respiratory mask of claim 19 wherein strengthening means comprise a plurality of spaced apart bosses, each of said bosses disposed opposite to each of said spaced apart openings of said anchoring means.

\* \* \* \* \*